(12) United States Patent
Daly

(10) Patent No.: US 8,357,136 B2
(45) Date of Patent: Jan. 22, 2013

(54) ENTERAL FEEDING SET

(75) Inventor: Paul J. Daly, Tullamore (IE)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 12/898,138

(22) Filed: Oct. 5, 2010

(65) Prior Publication Data

US 2011/0245771 A1    Oct. 6, 2011

Related U.S. Application Data

(63) Continuation of application No. 11/561,283, filed on Nov. 17, 2006, now Pat. No. 7,896,859, which is a continuation-in-part of application No. 11/254,520, filed on Oct. 20, 2005, now Pat. No. 7,611,502.

(51) Int. Cl.
*A61B 19/00* (2006.01)

(52) U.S. Cl. ........................................ 604/410; 604/411

(58) Field of Classification Search .................... 604/27, 604/82, 85, 88, 159, 249, 257, 408, 410, 604/411, 414, 416, 518, 910
See application file for complete search history.

(56) References Cited

U.S. PATENT DOCUMENTS

| | | |
|---|---|---|
| 3,467,270 A | 9/1969 | Eady |
| 3,542,240 A | 11/1970 | Solowey |
| 3,783,895 A | 1/1974 | Weichselbaum |
| 3,938,520 A | 2/1976 | Scislowicz et al. |
| 4,390,017 A | 6/1983 | Harrison et al. |
| 4,547,192 A | 10/1985 | Brodsky et al. |
| 4,613,323 A | 9/1986 | Norton et al. |
| 4,655,763 A | 4/1987 | Malcolm et al. |
| 4,683,424 A | 7/1987 | Cutright et al. |
| 4,688,595 A | 8/1987 | Srebnik et al. |
| 4,698,059 A | 10/1987 | Johnson |
| 4,699,296 A | 10/1987 | Schrock, Jr. |
| 4,713,064 A | 12/1987 | Bruno et al. |
| 4,781,704 A | 11/1988 | Potter |
| 4,787,890 A | 11/1988 | Ufermann |
| 4,826,500 A | 5/1989 | Rautsola |
| 4,828,550 A | 5/1989 | Kurimoto |
| 4,834,744 A | 5/1989 | Ritson |
| 4,863,424 A | 9/1989 | Blake, III et al. |
| 4,869,725 A | 9/1989 | Schneider et al. |

(Continued)

FOREIGN PATENT DOCUMENTS

| | | |
|---|---|---|
| DE | 8616731 U1 | 1/1987 |
| DE | 19807131 A1 | 8/1999 |

(Continued)

OTHER PUBLICATIONS

Office action dated Jun. 25, 2008 from related U.S. Appl. No. 11/254,520. 13 pgs.

(Continued)

*Primary Examiner* — Nicholas Lucchesi
*Assistant Examiner* — Gerald Landry, II

(57) ABSTRACT

The present invention provides an enteral feeding set comprising tubing adapted for fluid flow therethrough and further adapted to be engaged by a pump unit, a valve mechanism in direct communication with said tubing, said valve mechanism being adapted to be engaged by said pump unit, and a feeding set indicator for permitting identification of the functional configuration of said administration feeding set by said pump unit, characterized in that said tubing comprises at least two inlet tubes on an upstream side of said valve mechanism and a single outlet tube on a downstream side thereof and wherein said inlet tubes each include a connector for connecting said tube to a supply of fluid at a connection end thereof, each of said connectors being of like form but visually distinguishable for indicating to a user which supply of fluid each connector should be attached thereto.

23 Claims, 13 Drawing Sheets

U.S. PATENT DOCUMENTS

| | | |
|---|---|---|
| 4,871,359 A | 10/1989 | Sjonell |
| 4,886,504 A | 12/1989 | Arvidson et al. |
| 4,888,008 A | 12/1989 | D'Alo et al. |
| 4,895,275 A | 1/1990 | Quinn et al. |
| 4,909,797 A | 3/1990 | Timothy |
| 4,919,649 A | 4/1990 | Timothy et al. |
| 4,934,545 A | 6/1990 | Pezzoli et al. |
| 4,940,399 A | 7/1990 | Gorton et al. |
| 4,951,845 A | 8/1990 | Pezzoli et al. |
| 4,969,565 A | 11/1990 | Justal et al. |
| 4,997,429 A | 3/1991 | Dickerhoff et al. |
| 5,057,093 A | 10/1991 | Clegg et al. |
| 5,088,995 A | 2/1992 | Packard et al. |
| 5,122,123 A | 6/1992 | Vaillancourt |
| 5,125,522 A | 6/1992 | Pezzoli et al. |
| 5,125,897 A | 6/1992 | Quinn et al. |
| 5,137,527 A | 8/1992 | Miller et al. |
| 5,188,628 A | 2/1993 | Rani et al. |
| 5,224,932 A | 7/1993 | Lappas |
| 5,242,429 A | 9/1993 | Nwaneri et al. |
| 5,267,983 A | 12/1993 | Oilschlager et al. |
| 5,290,250 A | 3/1994 | Bommarito |
| 5,314,405 A | 5/1994 | Kriesel et al. |
| 5,332,113 A | 7/1994 | Kusler, III et al. |
| 5,336,188 A | 8/1994 | Kriesel |
| 5,336,203 A | 8/1994 | Goldhardt et al. |
| 5,372,578 A | 12/1994 | Kriesel et al. |
| 5,411,491 A | 5/1995 | Goldhardt et al. |
| 5,437,655 A | 8/1995 | Bartholomew |
| 5,458,583 A | 10/1995 | McNeely et al. |
| 5,498,253 A | 3/1996 | Aswad et al. |
| 5,569,209 A | 10/1996 | Roitman |
| 5,569,222 A | 10/1996 | Haselhorst et al. |
| 5,586,590 A | 12/1996 | Venooker et al. |
| 5,645,538 A | 7/1997 | Richmond |
| 5,665,064 A | 9/1997 | Bodicky et al. |
| 5,681,294 A | 10/1997 | Osborne et al. |
| 5,716,347 A | 2/1998 | Gibbs et al. |
| 5,720,734 A | 2/1998 | Copenhaver et al. |
| 5,730,418 A | 3/1998 | Feith et al. |
| 5,735,841 A | 4/1998 | Bourguignon et al. |
| 5,752,511 A | 5/1998 | Simmons et al. |
| 5,772,255 A | 6/1998 | Osborne et al. |
| 5,782,383 A | 7/1998 | Robinson |
| 5,836,924 A | 11/1998 | Kelliher et al. |
| 5,840,065 A | 11/1998 | Goldhardt et al. |
| 5,891,129 A | 4/1999 | Daubert et al. |
| 5,895,373 A | 4/1999 | Hirsch et al. |
| 5,924,584 A | 7/1999 | Hellstrom et al. |
| 5,925,011 A | 7/1999 | Faict et al. |
| 5,954,104 A | 9/1999 | Daubert et al. |
| 5,988,700 A | 11/1999 | Prichard |
| 6,012,596 A | 1/2000 | Oglesbee et al. |
| 6,056,724 A | 5/2000 | Lacroix |
| 6,066,112 A | 5/2000 | Quinn |
| 6,098,795 A | 8/2000 | Mollstam et al. |
| 6,139,534 A | 10/2000 | Niedospial, Jr. et al. |
| 6,165,168 A | 12/2000 | Russo |
| 6,173,199 B1 | 1/2001 | Gabriel |
| 6,182,698 B1 | 2/2001 | Barak |
| 6,183,465 B1 | 2/2001 | Meier et al. |
| 6,319,243 B1 | 11/2001 | Becker et al. |
| 6,332,467 B1 | 12/2001 | Hutson et al. |
| 6,364,143 B1 | 4/2002 | Knierbein |
| 6,371,319 B2 | 4/2002 | Yeaton et al. |
| 6,375,231 B1 | 4/2002 | Picha et al. |
| 6,394,993 B1 | 5/2002 | Chang et al. |
| 6,409,708 B1 | 6/2002 | Wessman |
| 6,471,676 B1 | 10/2002 | DeLegge et al. |
| 6,503,240 B1 | 1/2003 | Niedospial, Jr. et al. |
| 6,506,179 B1 | 1/2003 | Tiefenthal et al. |
| 6,551,299 B2 | 4/2003 | Miyoshi et al. |
| 6,568,439 B1 | 5/2003 | Se et al. |
| 6,582,395 B1 | 6/2003 | Burkett et al. |
| 6,602,239 B2 | 8/2003 | Ronneklev |
| 6,613,012 B2 * | 9/2003 | Kraushaar .................... 604/80 |
| 6,652,509 B1 | 11/2003 | Helgren et al. |
| 6,659,976 B2 | 12/2003 | Beck et al. |
| 6,678,553 B2 | 1/2004 | Lerner et al. |
| 6,709,424 B1 | 3/2004 | Knierbein |
| 6,752,790 B2 | 6/2004 | Coombs |
| 6,767,340 B2 | 7/2004 | Willis et al. |
| 6,769,539 B2 | 8/2004 | Stern et al. |
| 6,808,521 B1 | 10/2004 | McMichael |
| 6,875,204 B1 | 4/2005 | Hopkins et al. |
| 6,875,205 B2 | 4/2005 | Leinsing |
| 6,971,548 B2 | 12/2005 | Smith |
| 7,004,174 B2 | 2/2006 | Eggers et al. |
| 7,063,690 B2 | 6/2006 | Kessler et al. |
| 7,080,672 B2 | 7/2006 | Fournie et al. |
| 7,147,620 B2 | 12/2006 | Kessler et al. |
| 7,160,087 B2 | 1/2007 | Fathallah et al. |
| 7,165,910 B2 | 1/2007 | Sundheimer et al. |
| 7,219,819 B2 | 5/2007 | Halfacre et al. |
| 7,232,426 B2 | 6/2007 | Itrich et al. |
| 7,322,492 B2 | 1/2008 | Kawaguchi et al. |
| 7,381,204 B2 | 6/2008 | Wilson et al. |
| 7,455,662 B2 * | 11/2008 | Kraushaar .................... 604/189 |
| 7,462,170 B2 * | 12/2008 | Fournie et al. ................ 604/248 |
| 7,516,765 B2 | 4/2009 | Hogan et al. |
| 2002/0056989 A1 * | 5/2002 | Lewis-Leander ............... 283/81 |
| 2003/0006159 A1 | 1/2003 | Thorball et al. |
| 2003/0073971 A1 | 4/2003 | Saker |
| 2003/0075469 A1 | 4/2003 | Herbert |
| 2003/0088232 A1 | 5/2003 | Duell |
| 2003/0212381 A1 | 11/2003 | Whitehead, III |
| 2004/0011760 A1 | 1/2004 | Schupp et al. |
| 2004/0044327 A1 | 3/2004 | Hasegawa |
| 2004/0054350 A1 | 3/2004 | Shaughnessy et al. |
| 2004/0146341 A1 | 7/2004 | Sundheimer et al. |
| 2004/0153047 A1 * | 8/2004 | Blank et al. .................... 604/408 |
| 2004/0249350 A1 | 12/2004 | Rani |
| 2005/0033245 A1 | 2/2005 | Abrahamson et al. |
| 2005/0033267 A1 | 2/2005 | Decaria |
| 2005/0033268 A1 | 2/2005 | Decaria |
| 2005/0033269 A1 | 2/2005 | Decaria |
| 2005/0041888 A1 | 2/2005 | Matsuzawa et al. |
| 2005/0215943 A1 * | 9/2005 | Brandenburger et al. ...... 604/30 |
| 2005/0267418 A1 | 12/2005 | Fournie et al. |
| 2007/0060898 A1 | 3/2007 | Shaughnessy et al. |

FOREIGN PATENT DOCUMENTS

| | | |
|---|---|---|
| DE | 19842960 A1 | 3/2000 |
| DE | 20017609 U1 | 1/2001 |
| DE | 202004018089 U1 | 3/2005 |
| EP | 0119373 A1 | 9/1984 |
| EP | 0281270 B1 | 9/1988 |
| EP | 0355795 A1 | 2/1990 |
| EP | 0711538 B1 | 5/1996 |
| EP | 0729761 A | 9/1996 |
| EP | 0792631 A1 | 9/1997 |
| EP | 1010412 A2 | 6/2000 |
| EP | 1027900 A1 | 8/2000 |
| EP | 1384466 A1 | 1/2004 |
| EP | 1063956 B1 | 10/2004 |
| EP | 1 698 318 A1 | 9/2006 |
| WO | 9320772 | 10/1993 |
| WO | 9504564 | 2/1995 |
| WO | 9513105 | 5/1995 |
| WO | 9846293 A1 | 10/1998 |
| WO | 2004017852 A1 | 3/2004 |
| WO | 2004084793 A1 | 10/2004 |
| WO | 2005115501 A2 | 12/2005 |

OTHER PUBLICATIONS

Response filed Sep. 12, 2008 to Office Action dated Jun. 25, 2008 from related U.S. Appl. No. 11/254,520. 6 pgs.

Office action dated Apr. 2, 2009 from related U.S. Appl. No. 11/561,283. 10 pgs.

Response filed Aug. 5, 2009 to Office Action dated Apr. 2, 2009 from related U.S. Appl. No. 11/561,283. 11 pgs.

Office action dated Oct. 5, 2009 from related U.S. Appl. No. 11/561,283. 7 pgs.

Response filed Nov. 20, 2009 to Office Action dated Oct. 5, 2009 from related U.S. Appl. No. 11/561,283. 6 ps.

Office action dated Jul. 12, 2010 from related U.S. Appl. No. 11/561,283. 9 pgs.
Response filed Oct. 5, 2010 to Office Action dated Jul. 12, 2010 from related U.S. Appl. No. 11/561,283. 8 pgs.

European Search Report regarding related application serial No. EP 07120860.7 dated Jun. 22, 2012, 8 pgs.

* cited by examiner

ENTERAL FEEDING SET

CROSS REFERENCE TO RELATED APPLICATIONS

This application is a continuation application of application Ser. No. 11/561,283, filed Nov. 17, 2006, which is a continuation-in-part application of application Ser. No. 11/254,520 filed Oct. 20, 2005, now U.S. Pat. No. 7,611,502, the entirety of which is hereby incorporated by reference.

This Application claims priority to a pending U.S. Patent Application having Ser. No. 11/254,250 filed on 20 Oct. 2005. This Application is a Continuation in Part.

The present invention relates to an enteral feeding set and in particular an enteral feeding set for connection to an automatic pump system wherein a fluid to be supplied to a patient is automatically selectable from one of two fluid sources.

Feeding sets with more than one connection to a fluid source are known. For example, Tyco Healthcare has marketed an enteral feeding set (product code no. 717324) for connection to a pump having two tubes from two connectors leading to a single Y-connection. Each of the tubes may be individually clamped shut.

An enteral feeding set incorporating two fluid sources is shown in WO 2005/115501, the contents of which are incorporated by reference herein in their entirety. This document teaches the use of a flow control apparatus which controls the operation of a valve for selecting one of the fluid sources for fluid supply to a patient.

Another arrangement incorporating two fluid sources is described in WO 98/046293.

A wide variety of connectors for connecting enteral feeding sets to fluid sources are known. Examples include a sliding seal adapter described in WO 2004/017852 and a connector including a spike for piercing a foil seal described in EP 1 063 956.

It is an object of the invention to provide an enteral feeding set for connection to two different fluid sources in a manner such that a correct correction of a fluid source can be more reliably made.

SUMMARY OF THE INVENTION

The present invention provides in a first aspect an enteral feeding set comprising tubing adapted for fluid flow therethrough and further adapted to be engaged by a pump unit, a valve mechanism in direct communication with said tubing, said valve mechanism being adapted to be engaged by said pump unit, and a feeding set indicator for permitting identification of the functional configuration of said administration feeding set by said pump unit, characterized in that said tubing comprises at least two inlet tubes on an upstream side of said valve mechanism and a single outlet tube on a downstream side thereof and wherein said inlet tubes each include a connector for connecting said tube to a supply of fluid at a connection end thereof, each of said connectors being of like form but visually distinguishable for indicating to a user which supply of fluid each connector should be attached thereto.

In a second aspect, there is provided an enteral feeding set comprising tubing adapted for fluid flow therethrough and further adapted to be engaged by a pump unit, a valve mechanism in direct communication with said tubing, said valve mechanism being adapted to be engaged by said pump unit, and a feeding set indicator for permitting identification of the functional configuration of said administration feeding set by said pump unit, characterized in that said tubing comprises at least two inlet tubes on an upstream side of said valve mechanism and a single outlet tube on a downstream side thereof and wherein a first inlet tube includes a connector at a connection end thereof for connecting said first inlet tube to a substantially rigid fluid container and a second inlet tube is connected to a pliable fluid container.

The connectors of the enteral feeding sets of the invention may incorporate a projection for puncturing a seal on a fluid source in the form of a knife edge which punctures the seal and then, as the connector is being attached to the fluid source by means of a threaded coupling cuts the seal open to provide an opening in the seal which will not become blocked. Preferably, an air vent incorporating a microbial filter is also included. Sliding seal connectors may also be used.

In order to avoid an operator connecting fluid sources to the wrong tubing, the connectors may be colour coded such as to match a corresponding colour marking on a fluid container.

In a still further aspect of the invention, there is provided an enteral feeding set comprising a flush connector adapted to be coupled to a flush container holding a flush fluid therein, the flush connector comprising a first connector body, and a first liquid passage defined in the first connector body, the first liquid passage being in fluid communication with the flush container when the flush connector is coupled to the flush container, the first connector body further comprising a first spike extending outward for piercing a puncturable seal within the flush container, and a first air passage defined in the first connector body, the first air passage being coupled in fluid communication with the flush container for introducing air into the flush container; flush tubing coupled in fluid communication to the first liquid passage for receiving a flow of the flush fluid from the flush container; a feed connector adapted to be coupled to a feed container holding an enteral feed fluid therein, the feed connector comprising a second connector body, and a second liquid passage defined in the second connector body, the second liquid passage being in fluid communication with the feed container when the feed connector is coupled to the feed container, the second connector body further comprising a second spike extending outward for piercing a puncturable seal within the feed container, and a second air passage defined in the second connector body, the second air passage being coupled in fluid communication with the feed container for introducing air into the feed container; feed tubing coupled in fluid communication to the second liquid passage for receiving a flow of the enteral feed fluid from the feed container; and a valve having first and second inlets coupled in fluid communication with the feed and flush tubing, respectively, and a valve outlet, the valve being selectively operable to allow and block flow through the valve outlet.

In another aspect, there is provided an enteral feed set comprising a generally flexible flush bag adapted to hold a flush fluid therein; the flush tubing coupled in fluid communication with the flexible flush bag for receiving a flow of the flush fluid therefrom; a feed connector adapted to be coupled to a feed container holding an enteral feed fluid therein, the feed connector comprising a connector body, and a liquid passage defined in the connector body, the liquid passage being in fluid communication with the feed container when the feed connector is coupled to the feed container, the connector body further comprising a spike extending outward for piercing a puncturable seal within the feed container, and an air passage defined in the connector body, the air passage being coupled in fluid communication with the feed container for introducing air into the feed container; feed tubing coupled in fluid communication to the liquid passage of the feed connector for receiving a flow of the enteral feed fluid from the feed container; and a valve having first and second inlets coupled in fluid communication with the feed and flush tubing, respectively, and a valve outlet, the valve being selectively operable to allow and block flow through the valve outlet.

A further aspect of the invention is an enteral feed set comprising a flush adapter configured to be coupled in fluid communication to a flush container holding a flush fluid therein, the flush adapter comprising a first adapter body, a first spike member, a first spring, a first collar member, and a first sliding shaft seal, the first adapter body having a first annular flange, the first spike member being coupled with the first adapter body and including a first tube adapter, the first spring being disposed within the first adapter body for applying a spring force against the first spike member, the first collar member including a first annular groove configured to securely engage the first annular flange, the first sliding shaft seal being disposed at least partially within the first adapter body and being configured to slidingly engage in fluid tight engagement with the first spike member; flush tubing coupled in fluid communication to the first tube adapter for receiving a flow of the flush fluid from the flush container; a feed adapter configured to be coupled in fluid communication to a feed container holding an enteral feed fluid therein, the feed adapter comprising a second adapter body, a second spike member, a second spring, a second collar member, and a second sliding shaft seal, the second adapter body having a second annular flange, the second spike member being coupled with the second adapter body and including a second tube adapter, the second spring being disposed within the second adapter body for applying a spring force against the second spike member, the second collar member including a second annular groove configured to securely engage the second annular flange, the second sliding shaft seal being disposed at least partially within the second adapter body and being configured to slidingly engage in fluid tight engagement with the second spike member; feed tubing coupled in fluid communication to the second tube adapter for receiving a flow of the enteral feed fluid from the feed container; and a valve having first and second inlets coupled in fluid communication with the feed and flush tubing, respectively, and a valve outlet, the valve being selectively operable to allow and block flow through the valve outlet.

BRIEF INTRODUCTION TO THE DRAWINGS

Preferred embodiments of the present invention will now be described, by way of example only, with reference to the accompanying drawings in which.

DETAILED DESCRIPTION OF THE PREFERRED EMBODIMENTS

Figure 1:
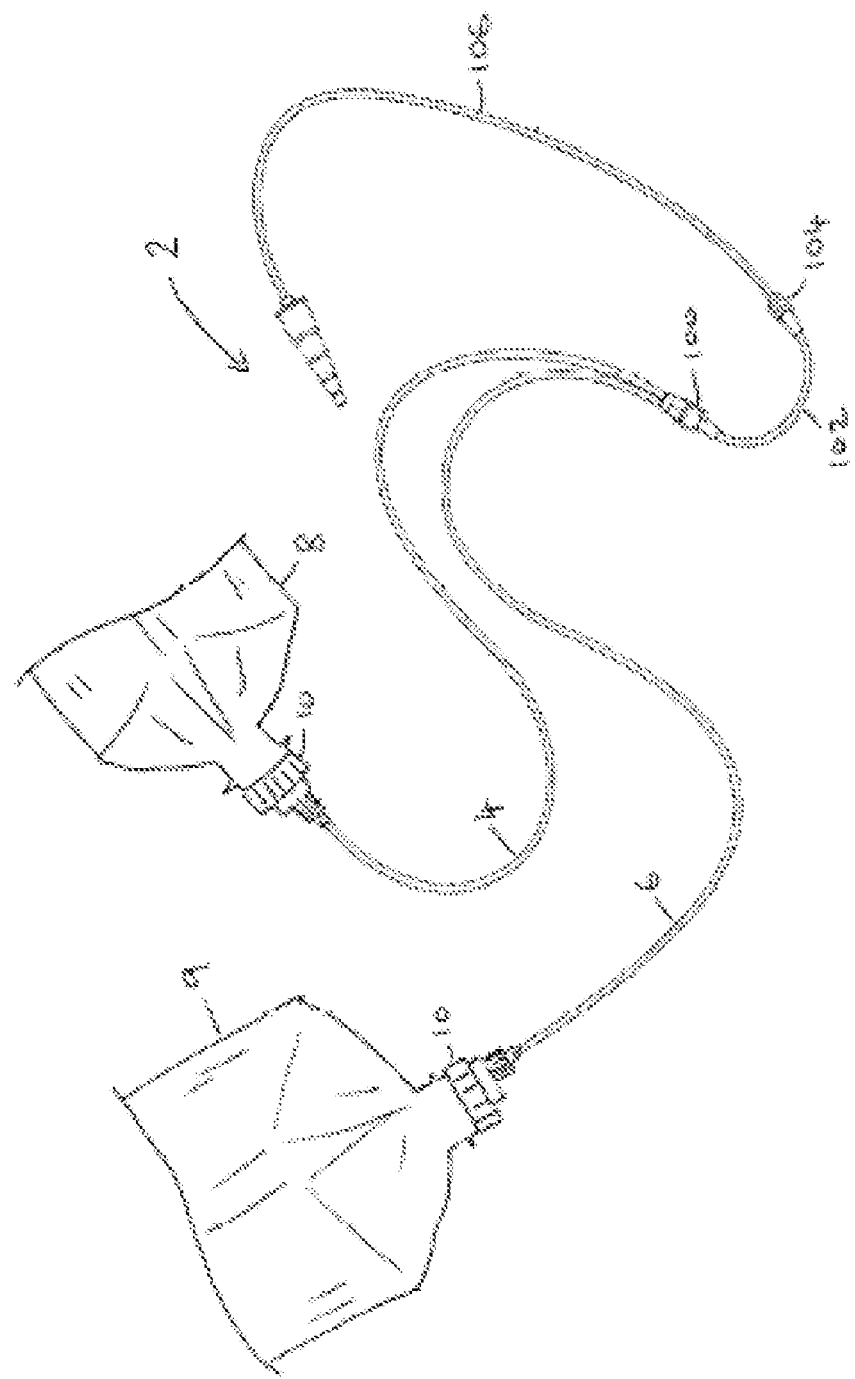
FIG. 1 is a schematic illustration of an enteral feed set for connection to two fluid sources.

FIG. 1 shows an enteral feeding set 2 having two tubes 4, 6 for connection to respective fluid sources 8, 9 by means of respective connectors 10.

Figure 2:
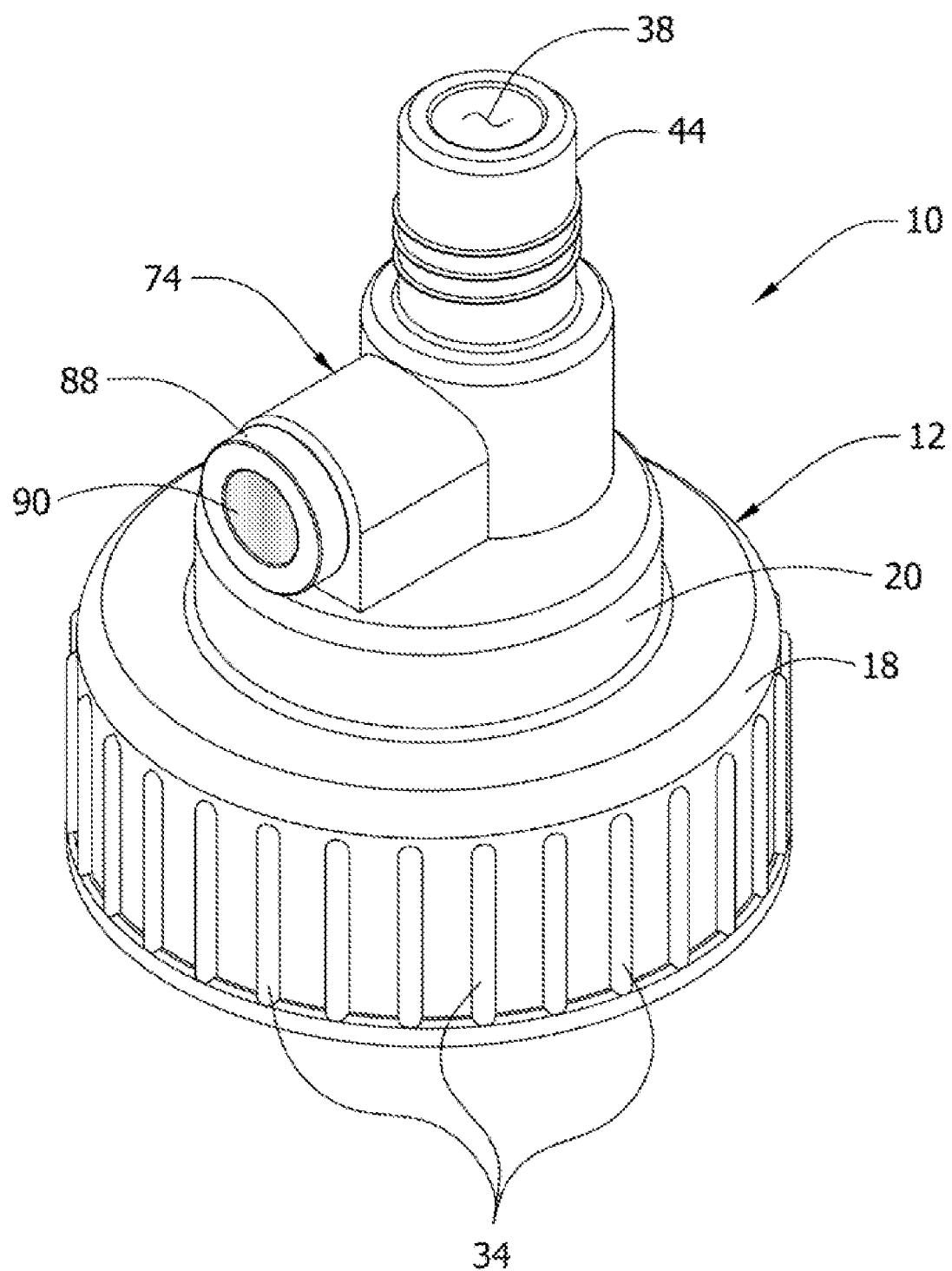
FIG. 2 is a perspective of a connector for connecting an enteral container of liquid nutrients to an enteral feeding tube.
Figure 3:
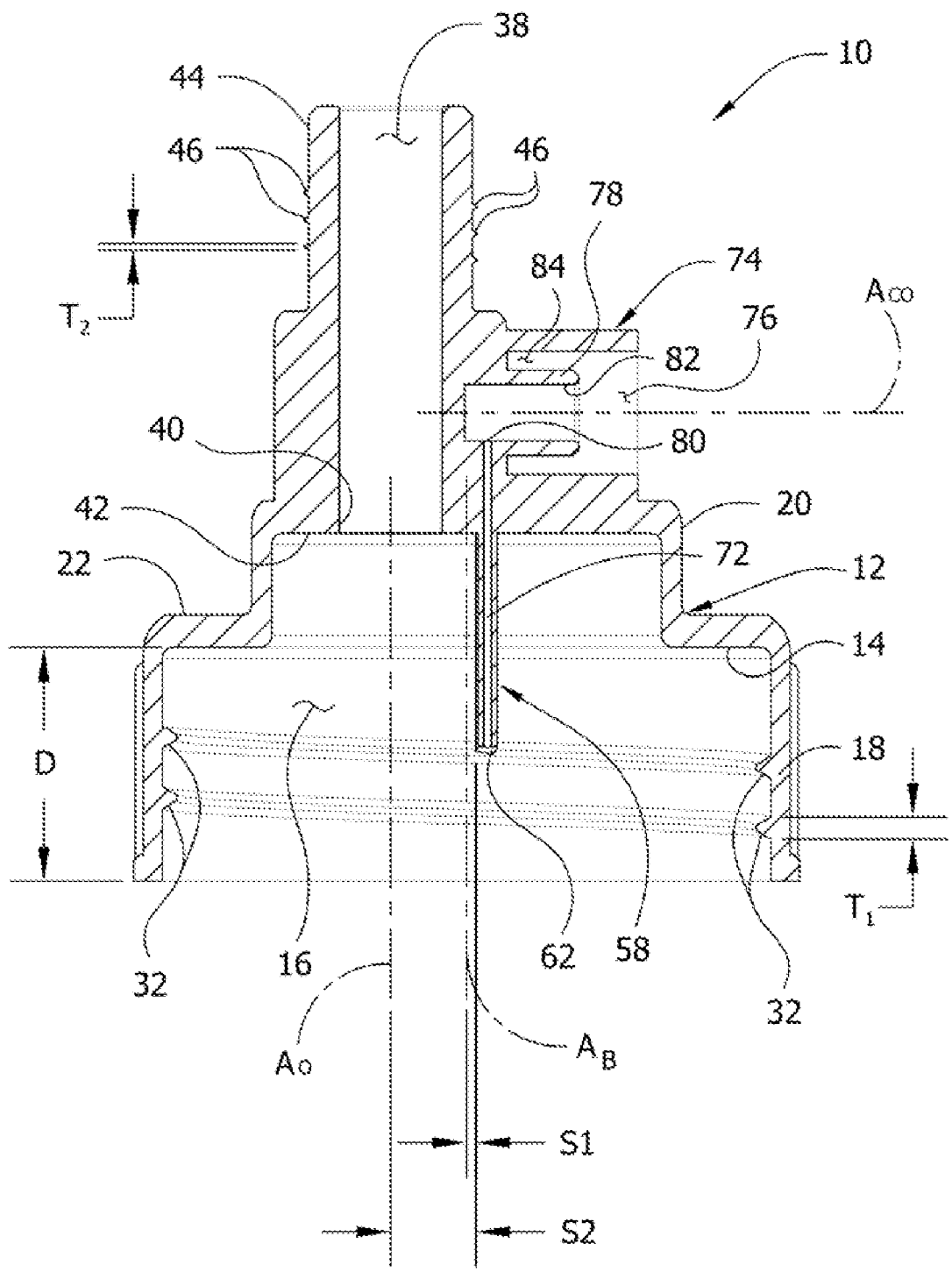
FIG. 3 is a vertical section of the connector.
Figure 4:
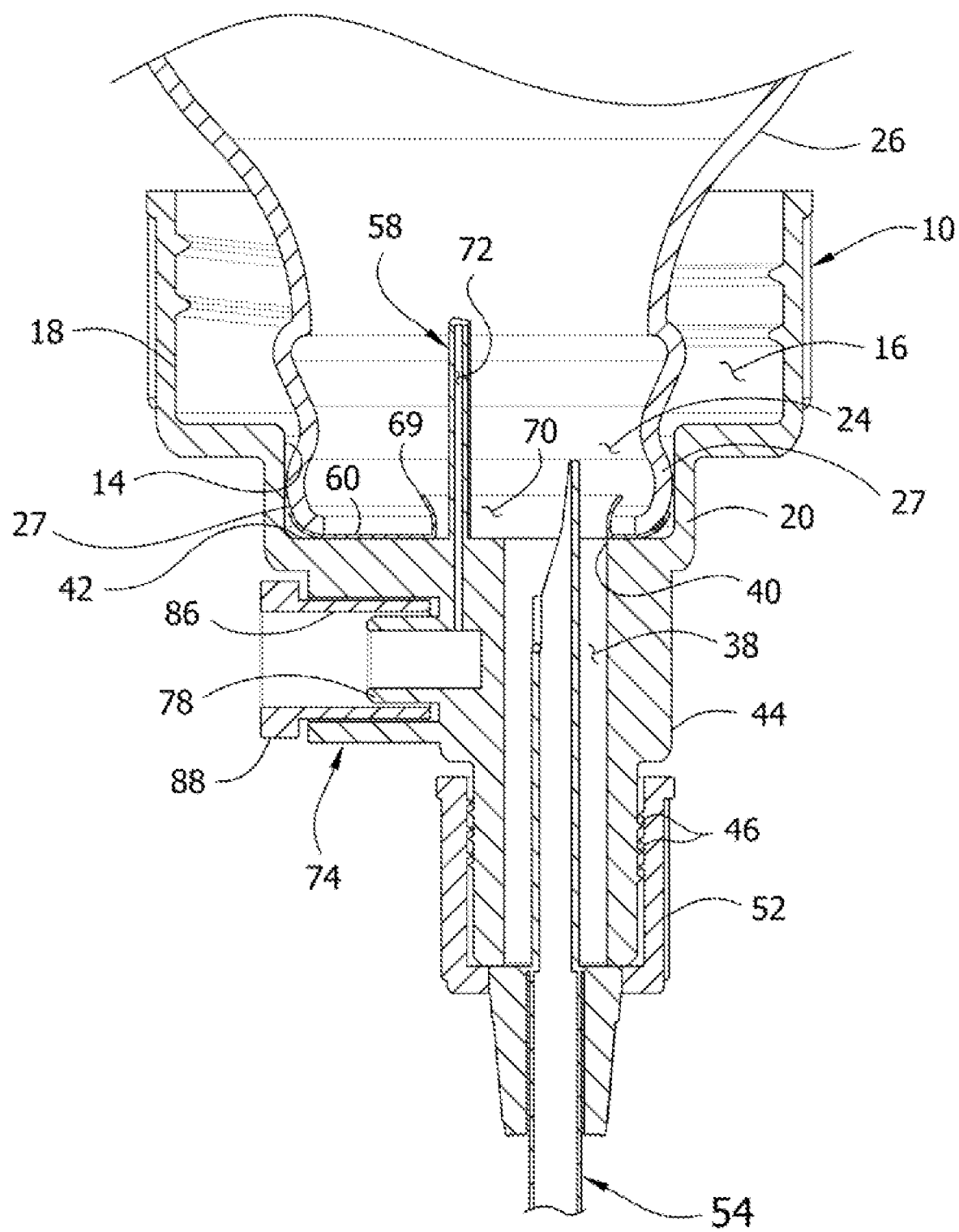
FIG. 4 is a vertical section of the connector snapped into to a small outlet container and attached to an enteral feeding tube.
Figure 5:
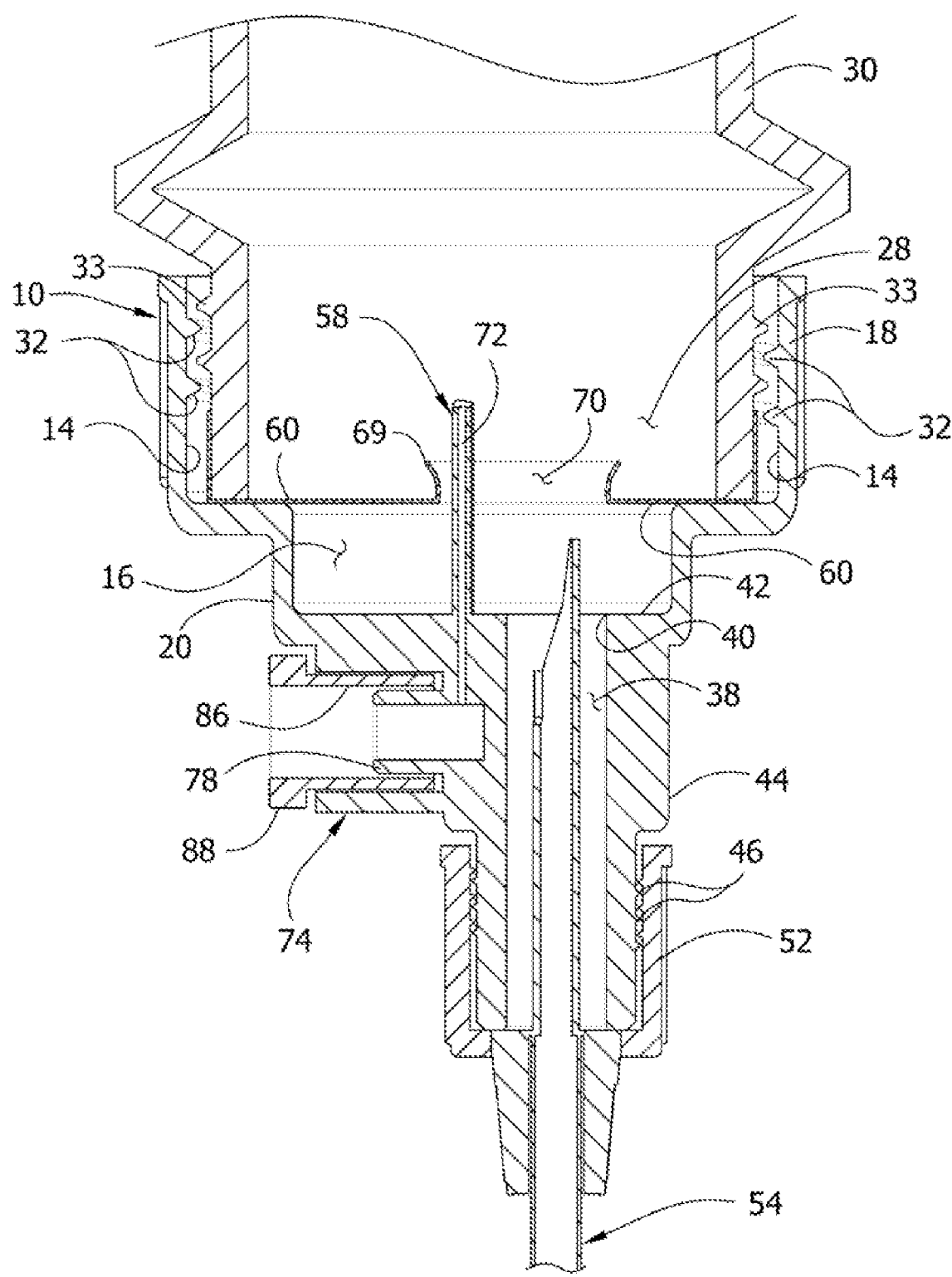
FIG. 5 is a vertical section of the connector threaded onto a large outlet container and attached to an enteral feeding tube.
Figure 6:
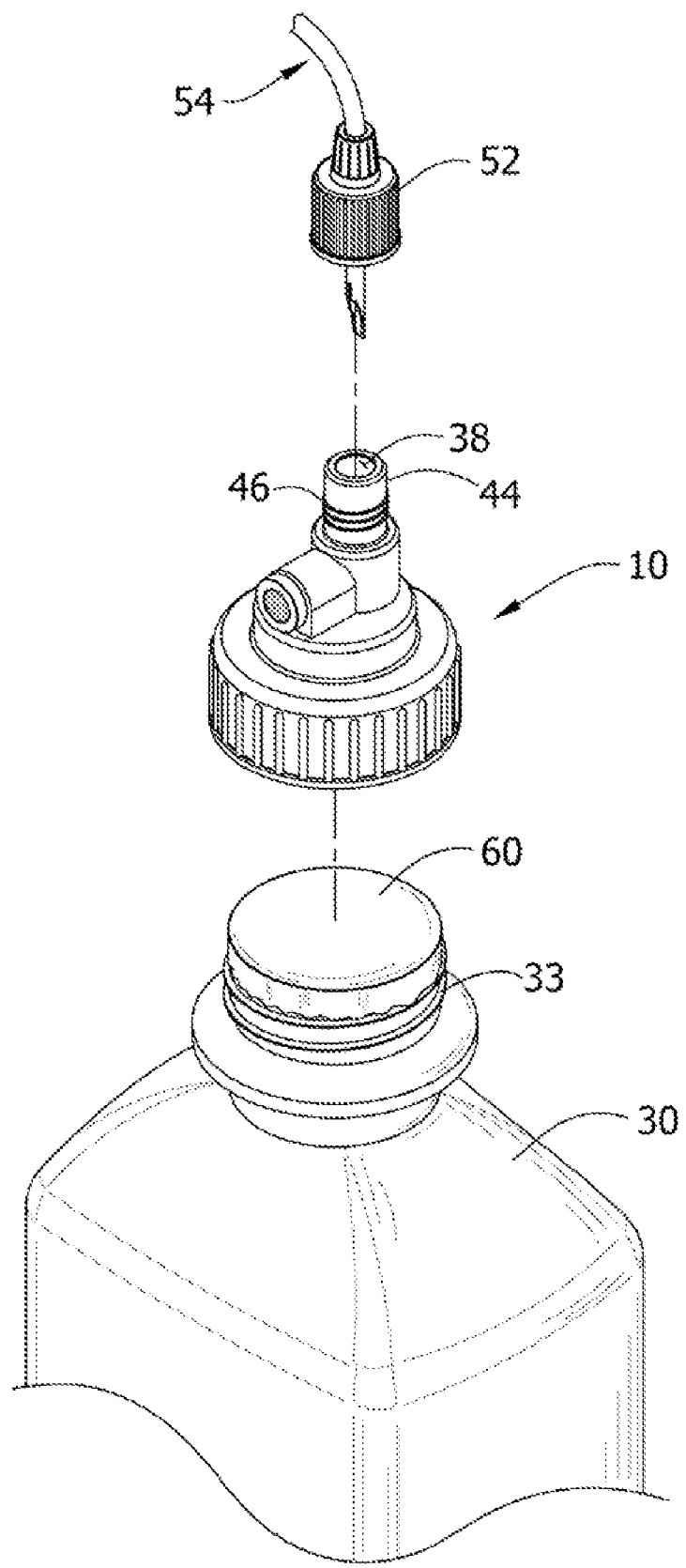
FIG. 6 is fragmentary exploded perspective of the large outlet container, the connector and the enteral feeding tube.

Referring now to FIGS. 2-3, the connector 10 is shown in more detail. The connector includes a body, generally indicated at 12, having an interior surface 14 (FIG. 3) that defines a cavity 16 for receiving an outlet of the container, as explained in more detail below (FIGS. 4-6). The body 12 has a cylindrical lower portion 18 and a smaller cylindrical upper portion 20 projecting upward from a top surface 22 of the lower portion.

Referring to FIGS. 4-6, the cavity 16 is configured for receiving different types of containers. As shown in FIG. 4, the cavity 16 at the upper portion 20 is sized and shaped for snap-fit reception of a relatively small outlet 24 of a container 26. The interior surface 14 at the upper portion 20 is elastically deformable to allow a rigid snap-fit member 27 (e.g., a projecting rim extending around the outlet 24) to snap-fit into the upper portion.

As shown in FIG. 5, the cavity 16 at the lower portion 18 is sized and shaped to threadably receive a relatively larger outlet 28 of a container 30. The interior surface 14 at the lower portion 18 of the connector 10 includes internally projecting threads 32 for attaching to external threads 33 extending around the outlet 28 of the container 30. The depth D (FIG. 3) of the cavity 16 at the lower portion 18 is between about 1.40 cm and 1.80 cm. This depth D allows the connector 10 to attach to containers 30 having necks of different sizes and accommodates a more secure connection with the different containers. Further, the internal threads 32 of the lower portion 18 have a thickness $T_1$ of between about 0.12 cm and about 0.11 cm. Ridges 34 (FIG. 2) disposed around an exterior surface of the body 12 at the lower portion 18 provide a user with adequate grip when threading the connector 10 on the container 30. The connector 10 may be configured to attach to an outlet of a container in other ways without departing from the scope of this invention. Moreover, the connector 10 may be configured to attach only to one type of container, such as a threaded container or a snap-fit container, or the connector may be configured to attach to more than two types of containers.

Referring to FIGS. 3-5, a liquid passage 38 extends through the upper portion 20 of the body 12 and is in fluid communication with the cavity 16. An opening 40 of the liquid passage 38 is substantially flush with an upper surface section 42 of the interior surface 14 of the body 12 (i.e., the liquid passage does not extend into the cavity 16), although it is contemplated that the liquid passage may extend into the cavity. In the illustrated embodiment, the upper surface section 42 is substantially flat. The liquid passage 38 also extends through a conduit 44 projecting outward from the exterior surface of the body 12 at the upper portion 20. The conduit 44 has externally projecting threads 46 for attaching to an internally threaded adapter 52 of an enteral feeding tube 54 (FIGS. 4-6). The external threads 46 of the conduit 44 have a thickness $T_2$ of between about 0.11 cm and about 0.06 cm. Other ways of connecting the enteral feeding tube 54 to the connector 10, including the use of an interference fitting, is within the scope of this invention.

As shown in FIGS. 4-6, when assembled, the connector 10 is secured to the outlet 24, 28 of the respective container 26, 30 by either threading (as shown in FIGS. 5 and 6) or fitting the connector on the container (FIG. 4). The threaded adapter 52 is threaded on the conduit 44 of the connector 10. Thus, when assembled, the connector 10 fluidly connects the enteral feeding tube 54 to the attached container 26, 30.

Figure 7:
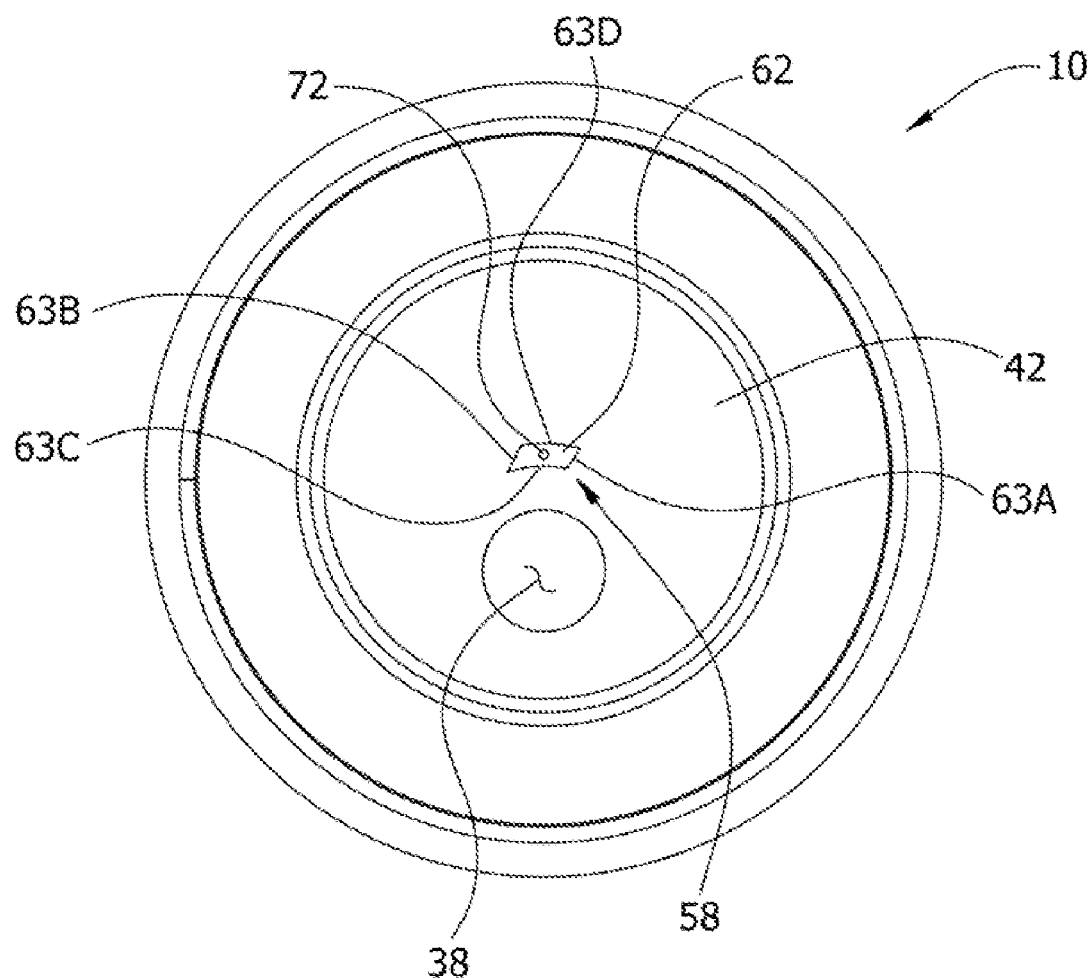
FIG. 7 is a bottom plan view of the connector.
Figure 8:
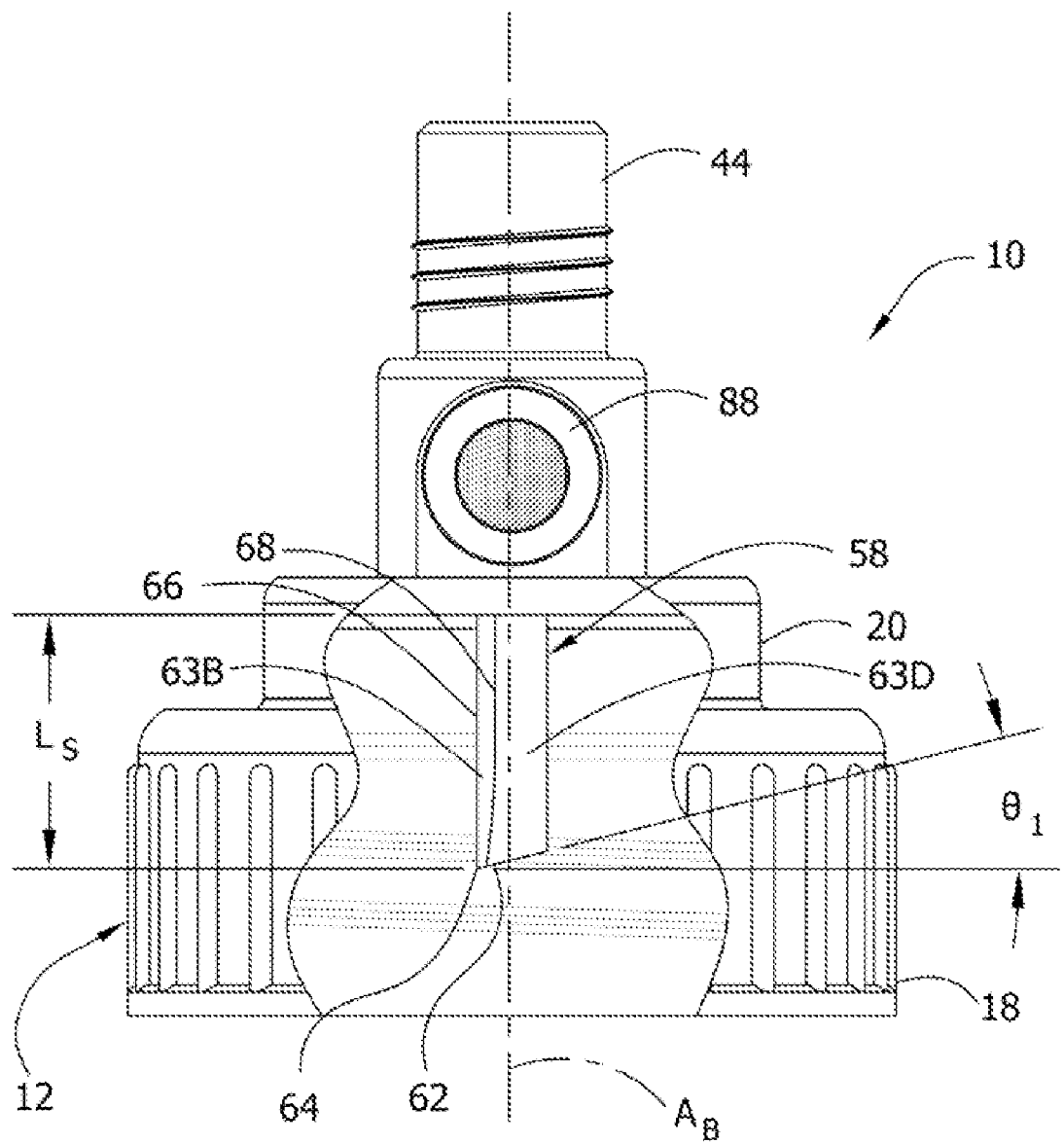
FIG. 8 is a front elevation of the connector with a portion of a body of the connector broken away to reveal a spike of the connector.

Referring to FIGS. 3-8, a generally elongate spike, generally indicated at 58, formed integrally with the body 12 projects from the upper surface section 42 of the body into the cavity 16. The spike 58 is spaced a distance $S_1$ (FIG. 3) from a central axis $A_B$ of the body 12 and a distance $S_2$ (FIG. 3) from a longitudinal axis $A_O$ of the opening 40 of the liquid passage 38. The spike 58 is configured to puncture a puncturable seal 60 (e.g., foil seal) (FIGS. 4-6) covering the outlet 24, 28 of the container 26, 30 to allow the liquid nutrients to exit the container. As shown best in FIG. 7, the spike 58 has a pair of opposite narrow sides 63A, 63B and a pair of opposite broad sides 63C, 63D extending between its length $L_S$ (FIG. 8).

Referring to FIGS. 7 and 8, a bottom surface 62 of the spike 58 (i.e., at the free end of the spike) is generally flat. As shown in FIG. 8, the bottom surface 62 is bevelled from the narrow side 63A (broadly, a first narrow side) to the opposite narrow side 63B (broadly, a second narrow side), such that the bottom surface lies in a plane intersecting the central axis $A_B$ of the body 12 at an angle $\theta_1$. This bevelled configuration of the bottom surface 62 forms a sharp tip 64 for puncturing the seal 60 of the threaded container 30. As shown in FIG. 8, the bottom surface 62 is also bevelled from the broad side 63C (broadly, a first broad side) to the opposite broad side 63D (broadly, a second broad side), such that the bottom surface lies in a plane intersecting the central axis of the body $A_B$ at an angle $\theta_2$.

Referring to FIG. 8, the narrow side 63B is bevelled from the broad side 63D to the opposite broad side 63C, defining a knife edge 66 along the length $L_S$ of the spike to the tip 64. After the seal 60 is punctured by the tip 64, the knife edge 66 cuts the seal 60 as the connector 10 is rotated (e.g., threaded) on the outlet 24, 28 of the container 26, 30. The spike 58 makes a relatively large (i.e., larger than the width of the spike 58), generally circular opening 70 through the seal, as illustrated in FIGS. 4 and 5.

Figure 9:
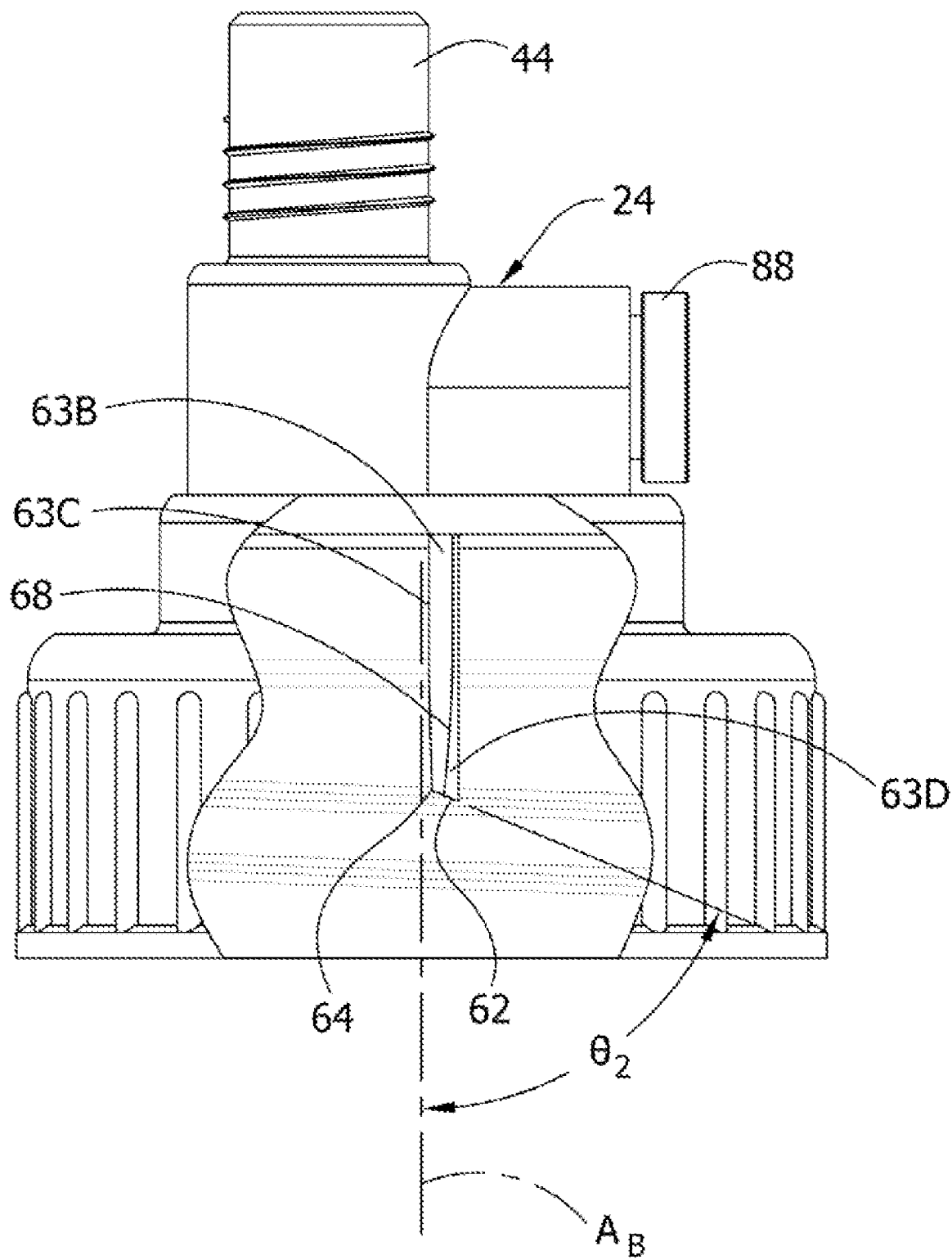
FIG. 9 is a side elevation of the connector with a portion of the body of the connector broken away to reveal the spike.

Referring to FIGS. 7-9, the broad side 63D of the spike 58 is generally arcuate and joins the bevelled narrow side 63B at folding edge 68. The narrow side 63B tapers toward the bottom surface 62 such that the folding edge 68 falls off or angles toward the tip 64. As the connector 10 is rotated on the container 26, 30, the knife edge 66 cuts the seal 60 and forms a foil edge margin 69 (FIGS. 3 and 4) defining the opening 70. Referring to FIGS. 4 and 5, as the connector 10 continues to rotate, the folding edge 68 of the spike 58 folds the foil edge margin 68 of the seal 60 away from the opening 70 in the seal 60 and away from the opening 40 of the liquid passage 38 so that the foil edge margin will not obstruct the openings.

Referring to FIGS. 3-5, an air passage 72 extends from the cavity 16 through the spike 58 and the upper portion 20 of the body 12. A vacuum within the container 26, 30, created when the liquid exits the container, draws air into the container through the air passage 72, thereby allowing the liquid to flow continuously and freely out of the container through the liquid passage 38 of the connector 10. The air passage 72 opens at the bottom surface 62 of the spike 58 to communicate with the cavity 16, although the passage may open at other locations along the length $L_S$ of the spike.

Figure 10:
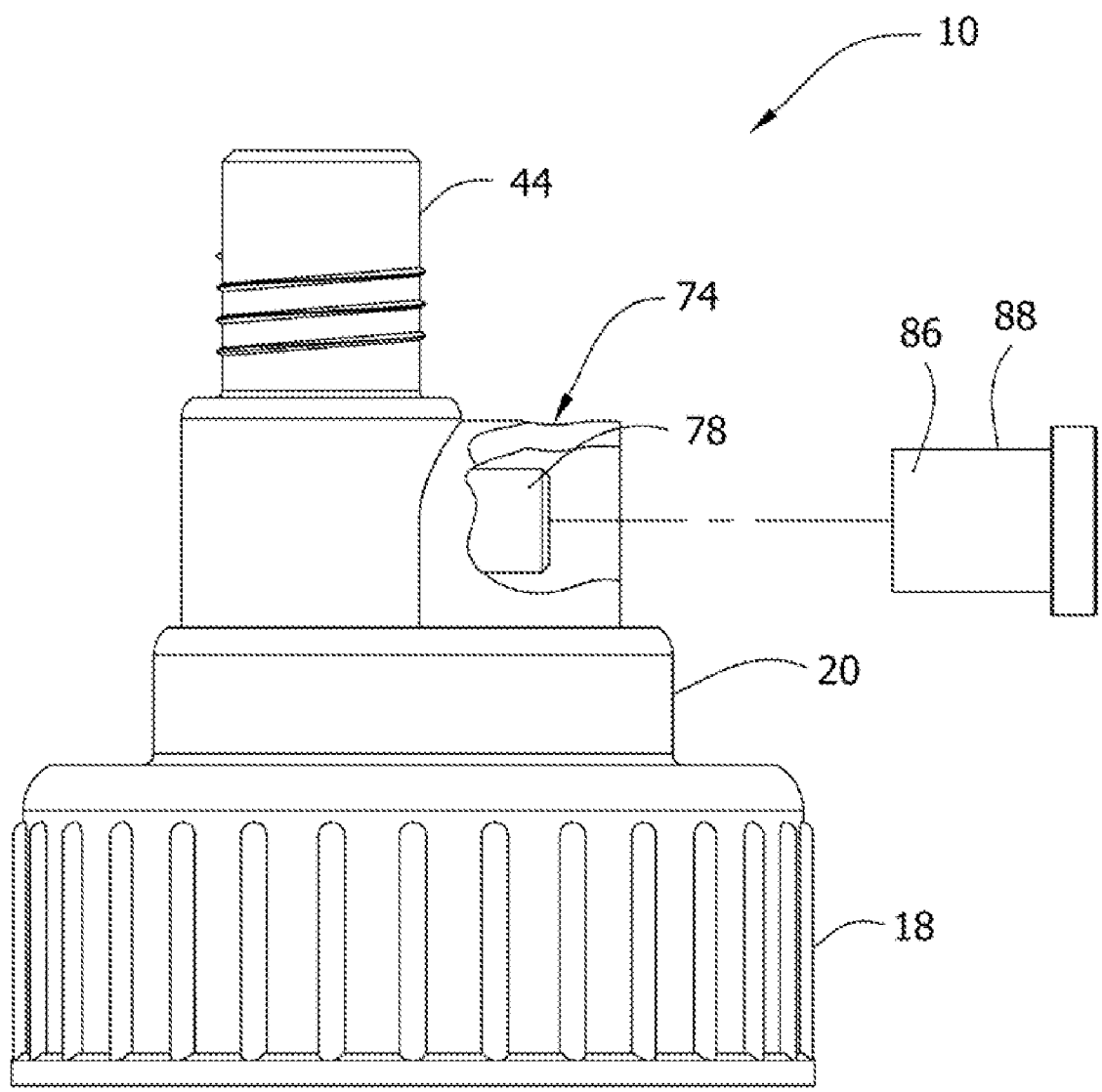
FIG. 10 is a side elevation of the connector with an air filter exploded from the connector and a mount for the filter partially broken to illustrated internal

Referring to FIGS. 3-5 and 9, the air passage 72 is fluidly connected to a filter mount, generally indicated at 74, projecting outward from the exterior surface of the body 12 at the upper portion 20. The filter mount 74 includes a large cylindrical opening 76 (FIG. 3) having a longitudinal axis $A_{CO}$ extending generally transverse to the central axis $A_B$ of the body 12. A tubular duct 78 disposed within the large opening 76 extends generally coaxially therein. As shown in FIG. 3, the duct 78 has a first open end 80 in fluid communication with the air passage 72 and a second open end 82 terminating within the large opening 76. The large opening 76 and an exterior surface of the duct 78 define an annular socket 84 (FIG. 3) making an interference fit with a tubular end 86 of a filter 88 (FIG. 10) such that the filter is in fluid communication with the duct and the air passage 72 when fitted in the socket. As shown in FIGS. 2, 4 and 5, when the air filter 88 is received in the filter mount 74, a filter medium 90 of the filter extends outside the mount.

The entire connector 10, excluding the air filter 88, may be formed as a homogeneous and integral unit, such as by molding (e.g., injection molding) or by forming, including boring, from stock material. Alternatively, the connector 10 may be constructed of one or more separate components fastened together in a suitable manner. Suitable materials for making the connector 10 include polypropylene (e.g., polypropylene 535), polyethylene and other suitable polymers. Other material may be used, and different material may be used for the separate components of the connector 10.

Referring again to FIG. 1, the connectors 10 are connected to first ends of respective tubes 4 and 6. These tubes are connected at their opposite ends to a valve unit 100 which also connects to a single tube 102 at a first end thereof. The tube 102 is attached to an automated peristaltic pump (not shown) which as well as controlling the pumping of fluid through the feeding set 2 operates the valve unit 100. A magnetic feed set identifier 104 is attached to a second end of the tube 102 and a further tube 106 leads therefrom for connection to a patient-indwelling gastrostomy device (not shown). Details of a suitable automated pump arrangement are described in WO 2005/115501, the contents of which are incorporated herein by reference.

Fluid sources are attachable to the connectors 10. In the preferred embodiment, fluid sources 8 and 9 may be connected, in which fluid source 8 contains a feeding solution and fluid source 9 contains a flushing solution.

In view of the automated operation of the pump, it is important that an operator correctly connects the fluid sources to the feed set in order that the automatic pump controls the valve appropriately. In order to ensure correct matching of a particular connector 10 to a particular fluid source, in the preferred embodiment, the connectors are colour coded such that a colour of the plastic molding of the body 12 of the connector corresponds to a colour of the fluid source container, whereby the container may, for example, be appropriately coloured by colouring a screw fitting molding to which the connector 10 is attached or by a coloured foil around the fluid container. Rather than colouring the connector 10, a coloured flag could be attached to the appropriate tube 4 and 6 for matching with an appropriate coloured container.

Figure 11:
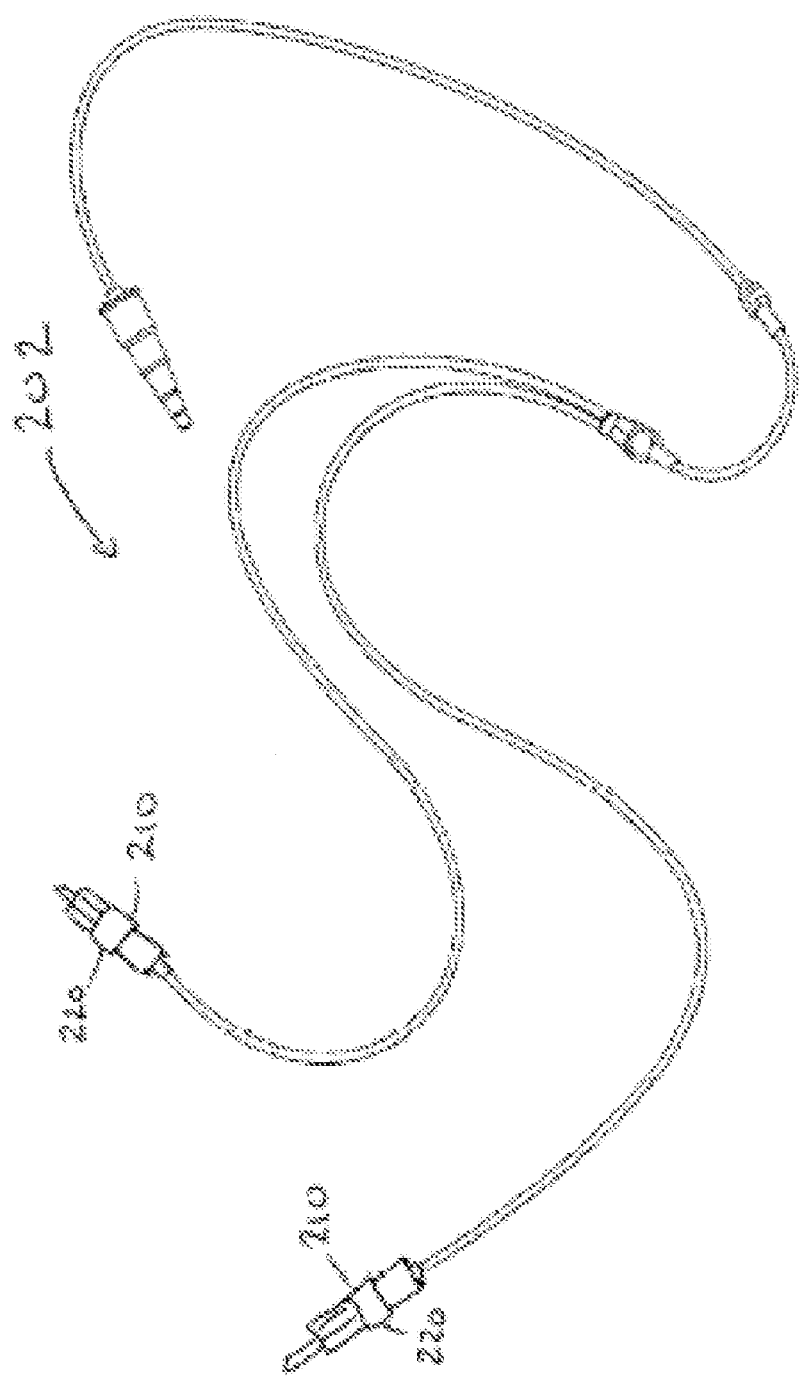
FIG. 11 is a schematic illustration of a second enteral feeding set
Figure 12:
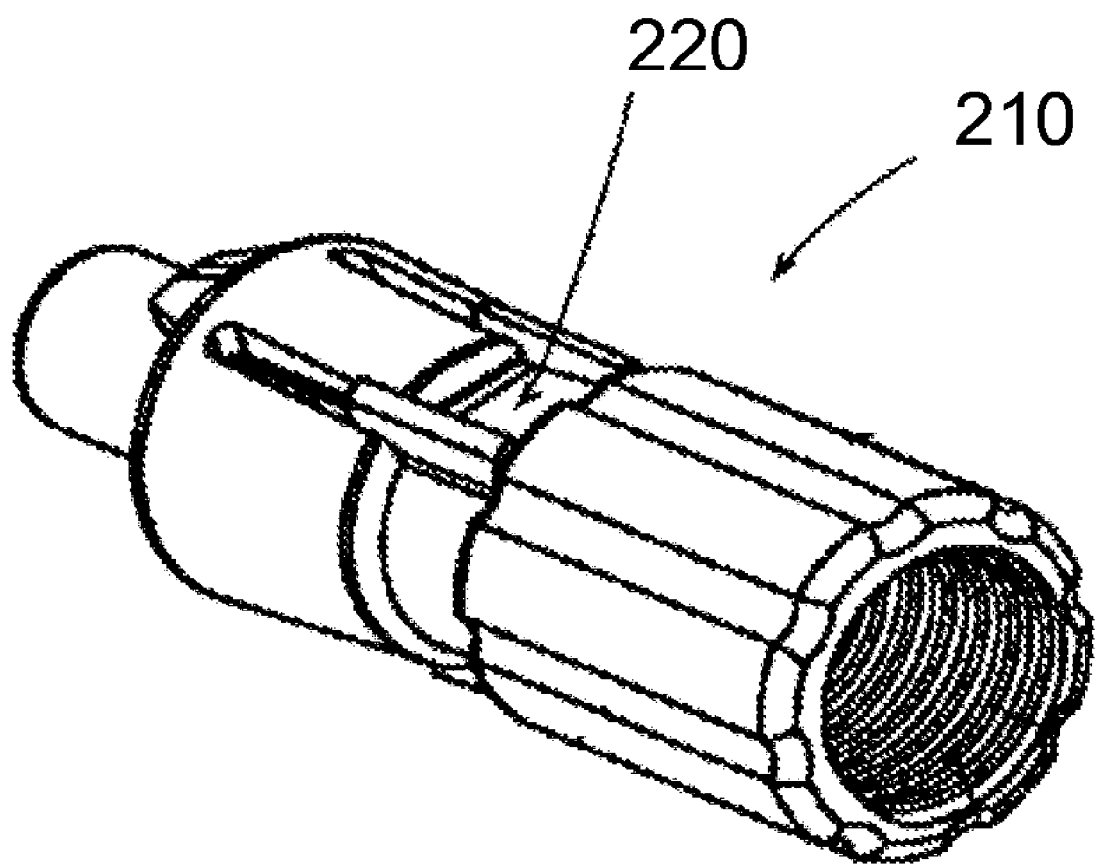
FIG. 12 shows a sliding seal connector.

Another solution for providing an improved enteral feeding set is an arrangement as shown in FIG. 11. In the arrangement of FIG. 11, rather than the connectors 10 of the FIG. 1 arrangement, the enteral feeding set 202 shown in FIG. 11 includes two sliding seal connectors 210. The sliding seal connectors 210 are fabricated in accordance with the arrangement shown in WO 2004/017852. An expanded view of one of the connectors 210 is shown in FIG. 12. As in the case of the feeding set 2, the feeding set 202 provides means for correctly matching up a respective connector 210 to a respective fluid source. The preferred means in the case of the arrangement shown in FIG. 11 is to colour code one of the components forming the connector, for example a body portion 220. Of course, a coloured flag arrangement could also be used, as with the arrangement of FIG. 1.

Figure 13:
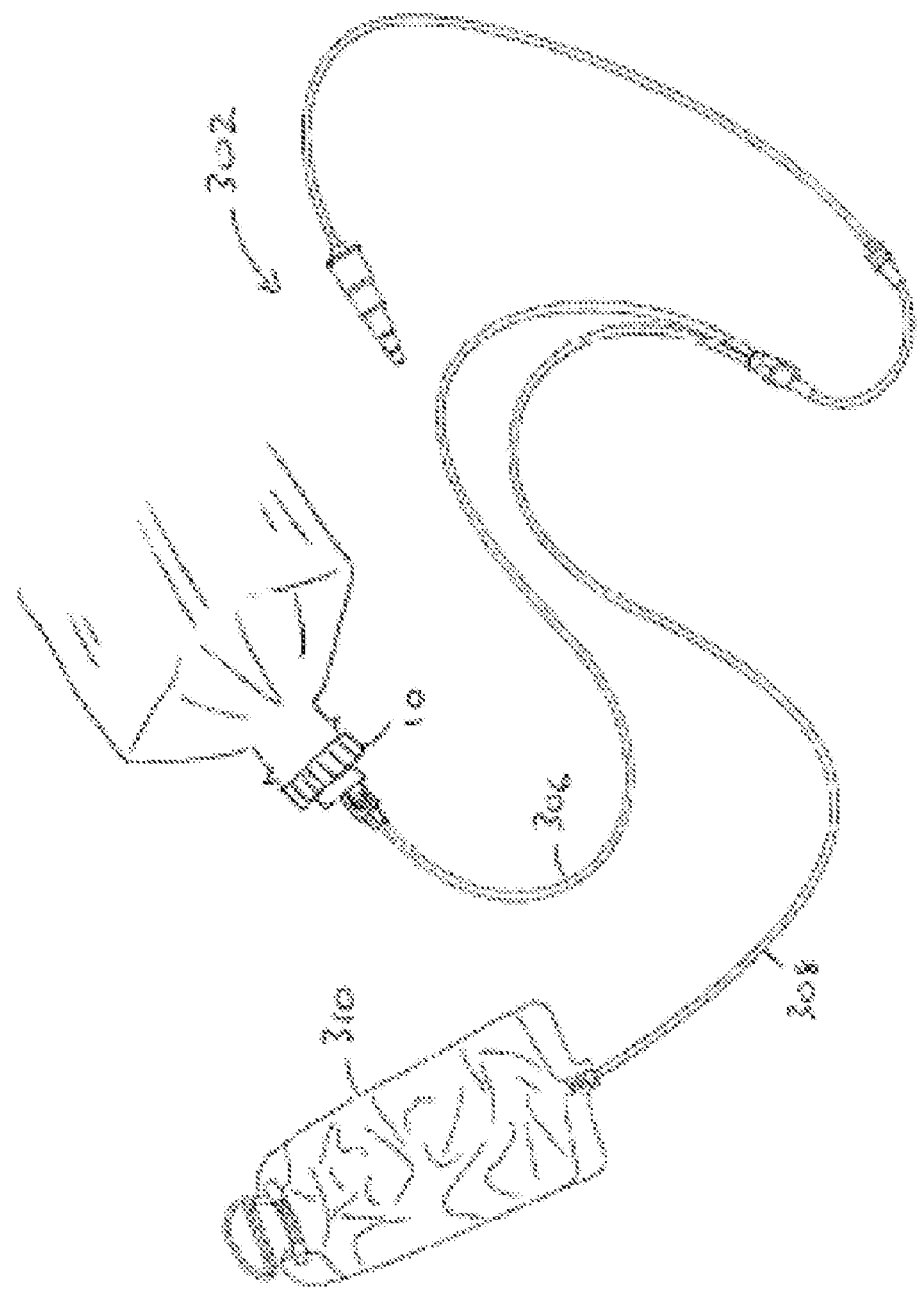
FIG. 13 is a schematic illustration of a third enteral feeding set.

A still further solution for providing an improved enteral feeding set is an arrangement as shown in FIG. 13. In this arrangement, the enteral feeding set 302 incorporates a single connector 10 in accordance with the connector shown in FIGS. 2-10 attached to one tube 306. Second tube 308 terminates in a permanent connection to a refillable fluid bag 310. By providing two different fluid sources, one a rigid container containing a feeding solution and a refillable bag for receiving a flushing solution, the arrangement of FIG. 13 provides an enhanced degree of security that the correct fluid solution will be provided to the correct connection tube.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. An enteral feeding set in combination with supplies of fluid comprising:
   supplies of fluid, each supply of fluid having a visually distinguishing element matching a respective connector, the element being non-removably attached to the supply of fluid,
   tubing adapted for fluid flow therethough and further adapted to be engaged by a pump unit,
   a valve mechanism in direct communication with said tubing, said valve mechanism being adapted to be engaged by said pump unit, and
   a feeding set indicator for permitting identification of the functional configuration of said administration feeding set by said pump unit, said tubing comprising at least two inlet tubes on an upstream side of said valve mechanism and a single outlet tube on a downstream side thereof and wherein each inlet tube includes a connector for connecting said tube to a supply of fluid at a connection end thereof, each of said connectors comprising at least a part of the feeding set indicator and being of like form but visually distinguishable for indicating to a user which supply of fluid each connector should be attached thereto.

2. The feeding set according to claim 1, wherein said connectors each comprise:
   a body having an interior surface defining a cavity for receiving an outlet of the container, and an exterior surface;
   a liquid passage defined in the body having a first end in fluid communication with the cavity and a second end for connection to the enteral feeding tube to fluidly connect the container and the enteral feeding tube when the connector is received on the container;
   a spike formed integrally with the body and having a free end projecting into the cavity for piercing a puncturable seal covering the outlet of the container as the outlet of the container is being received in the cavity;
   an air passage extending though the spike to the exterior surface of the body for introducing air from outside the connector into the container when the connector is attached to the container; and
   the body being free of structure that both defines any portion of the liquid passage and is formed for penetrating the puncturable seal of the container.

3. The feeding set according to claim 2 wherein the interior surface of the body includes an upper surface section, the liquid passage having an opening generally flush with the upper surface section, and further wherein no portion of the liquid passage extends into the cavity.

4. The feeding set according to claim 2 further comprising an air filter and a filter mount disposed on the exterior surface of the body in fluid communication with the air passage for connecting the air filter to the body.

5. The feeding set according to claim 2 wherein the body has a cylindrical lower portion and a cylindrical upper portion projecting from the lower portion, the interior surface at the lower portion having internally projecting threads for threadably attaching to a container with a threaded, larger diameter outlet, the interior surface at the upper portion being adapted for snap fitting to a container with a smaller diameter outlet.

6. The feeding set according to claim 2 wherein the spike has a generally flat bottom surface and the air passage opens at the flat bottom surface into the cavity.

7. The feeding set according to claim 2 wherein the spike has first and second opposite broad sides, and first and second opposite narrow sides, the second narrow side being beveled from the second broad side to the first broad side, so that a cutting edge is formed where the second narrow side meets the first broad side, the second narrow side tapering toward the free end of the spike such that a folding edge is formed where the second narrow side meets the second broad side.

8. The feeding set according to claim 1 wherein each connector comprises an internally threaded body for attaching the connector to a fluid container and a spike member arranged within said internally threaded body and attached to a body member slidably movable along a shaft seal.

9. An enteral feeding set comprising:
   tubing adapted for fluid flow therethough and further adapted to be engaged by a pump unit,
   a valve mechanism in direct communication with said tubing, said valve mechanism being adapted to be engaged by said pump unit, and
   a feeding set indicator for permitting identification of the functional configuration of said administration feeding set by said pump unit, said tubing comprising at least two inlet tubes on an upstream side of said valve mechanism and a single outlet tube on a downstream side thereof and wherein each inlet tube includes a connector for connecting said tube to a supply of fluid at a connection end thereof, each of said connectors comprising at least a part of the feeding set indicator and being of like form but visually distinguishable for indicating to a user which supply of fluid each connector should be attached thereto,
   wherein one of said connectors comprises a flush connector adapted to be coupled to a flush container holding a flush fluid therein, the flush connector comprising a first connector body, and a first liquid passage defined in the first connector body, the first liquid passage being in fluid communication with the flush container when the flush connector is coupled to the flush container, the first connector body further comprising a first spike extending outward for piercing a puncturable seal within the flush container, and a first air passage defined in the first connector body, the first air passage being coupled in fluid communication with the flush container for introducing air into the flush container;

wherein one of the inlet tubes comprises flush tubing coupled in fluid communication to the first liquid passage for receiving a flow of the flush fluid from the flush container;

wherein the other of the connectors comprises a feed connector adapted to be coupled to a feed container holding an enteral feed fluid therein, the feed connector comprising a second connector body, and a second liquid passage defined in the second connector body, the second liquid passage being in fluid communication with the feed container when the feed connector is coupled to the feed container, the second connector body further comprising a second spike extending outward for piercing a puncturable seal within the feed container, and a second air passage defined in the second connector body, the second air passage being coupled in fluid communication with the feed container for introducing air into the feed container; and wherein the other of the inlet tubes comprises:
feed tubing coupled in fluid communication to the second liquid passage for receiving a flow of the enteral feed fluid from the feed container; and
a valve having first and second inlets coupled in fluid communication with the feed and flush tubing, respectively, and a valve outlet, the valve being selectively operable to allow and block flow through the valve outlet.

10. The set of claim 9, wherein at least one of the first and second connector bodies includes a cavity and a base, the respective air passage extending upward from the base into the cavity.

11. An enteral feeding set comprising:
tubing adapted for fluid flow therethough and further adapted to be engaged by a pump unit,
a valve mechanism in direct communication with said tubing, said valve mechanism being adapted to be engaged by said pump unit, and
a feeding set indicator for permitting identification of the functional configuration of said administration feeding set by said pump unit, said tubing comprising at least two inlet tubes on an upstream side of said valve mechanism and a single outlet tube on a downstream side thereof and wherein each inlet tube includes a connector for connecting said tube to a supply of fluid at a connection end thereof, each of said connectors comprising at least a part of the feeding set indicator and being of like form but visually distinguishable for indicating to a user which supply of fluid each connector should be attached thereto, and
a generally flexible flush bag adapted to hold a flush fluid therein;
wherein one of the inlet tubes comprises flush tubing coupled in fluid communication with the flexible flush bag for receiving a flow of the flush fluid therefrom;
wherein one of the connectors comprises a feed connector adapted to be coupled to a feed container holding an enteral feed fluid therein, the feed connector comprising a connector body, and a liquid passage defined in the connector body, the liquid passage being in fluid communication with the feed container when the feed connector is coupled to the feed container, the connector body further comprising a spike extending outward for piercing a puncturable seal within the feed container, and an air passage defined in the connector body, the air passage being coupled in fluid communication with the feed container for introducing air into the feed container; and wherein the other of the inlet tubes comprises:
feed tubing coupled in fluid communication to the liquid passage of the feed connector for receiving a flow of the enteral feed fluid from the feed container; and
a valve having first and second inlets coupled in fluid communication with the feed and flush tubing, respectively, and a valve outlet, the valve being selectively operable to allow and block flow through the valve outlet.

12. The set of claim 11, wherein the connector body includes a cavity and a base, the air passage extending upward from the base into the cavity.

13. The set of claim 12, wherein the air passage is spaced apart from the liquid passage along an interior surface of the connector body.

14. The set of claim 12, wherein the spike is located along the base adjacent to the liquid passage.

15. The set of claim 12, wherein the air passage stem has an outer end located within the cavity.

16. The set of claim 12, wherein the connector body includes a connection portion adapted to be connected to the feed container, the liquid passage extends through the base and comprises an inlet for receiving fluid from the cavity, and the air passage extends toward the connection portion from an end coupled to the base to a free end located within the cavity, wherein the air passage is closer to the connection portion than the liquid passage inlet.

17. The set of claim 11, wherein the feed connector is configured to be threadably connected to the feed container.

18. The set of claim 11, in combination with the feed container, wherein the feed container comprises a generally rigid container.

19. The set of claim 11, in combination with the feed container, wherein the feed container comprises a generally flexible bag.

20. The set of claim 11, further comprising a pump tube coupled in fluid communication with the valve outlet, the pump tube being adapted to be acted upon to pump fluid received from the valve through the pump tube.

21. The feeding set according to claim 1, further comprising an indicator element on each connector corresponding to a matching indicator element associated with a respective fluid supply.

22. An enteral feeding set comprising:
tubing adapted for fluid flow therethough and further adapted to be engaged by a pump unit,
a valve mechanism in direct communication with said tubing, said valve mechanism being adapted to be engaged by said pump unit,
and a feeding set indicator for permitting identification of the functional configuration of said administration feeding set by said pump unit, said tubing comprising at least two inlet tubes on an upstream side of said valve mechanism and a single outlet tube on a downstream side thereof and wherein each inlet tube includes a connector for connecting said tube to a supply of fluid at a connection end thereof, the feeding set indicator comprising an indicator flag on each inlet tube corresponding to a matching indicator element associated with a respective fluid supply, the indicator element being non-removably attached to the fluid supply.

23. The feeding set according to claim 1, wherein the connectors form no part of a drip chamber.

* * * * *